United States Patent
Kanikanti et al.

(10) Patent No.: US 10,251,932 B2
(45) Date of Patent: *Apr. 9, 2019

(54) PREPARATIONS CONTAINING AMORPHOUS EMODEPSIDE

(71) Applicant: Bayer Intellectual Property GmbH, Monheim (DE)

(72) Inventors: Venkata-Rangarao Kanikanti, Leverkusen (DE); Petra Lange, Essen (DE); Hans-Juergen Hamann, Dormagen (DE); Peter Kleinebudde, Düsseldorf (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/803,445

(22) Filed: Nov. 3, 2017

(65) Prior Publication Data

US 2018/0153957 A1 Jun. 7, 2018

Related U.S. Application Data

(63) Continuation of application No. 15/397,923, filed on Jan. 4, 2017, which is a continuation of application No. 14/365,841, filed as application No. PCT/EP2012/075909 on Dec. 18, 2012, now Pat. No. 9,539,331.

(30) Foreign Application Priority Data

Dec. 21, 2011 (EP) .................................... 11194878

(51) Int. Cl.
*A61K 9/14* (2006.01)
*A61K 38/15* (2006.01)
*A61K 47/32* (2006.01)

(52) U.S. Cl.
CPC .............. *A61K 38/15* (2013.01); *A61K 9/146* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 5,514,773 A | 5/1996 | Nishiyama et al. | |
| 7,914,816 B2 | 3/2011 | Kalbe et al. | |
| 9,539,331 B2 | 1/2017 | Kanikanti | |
| 2003/0109639 A1 | 6/2003 | Lippold | |
| 2011/0046072 A1* | 2/2011 | Kanikanti | A61K 9/0056 514/21.1 |
| 2012/0141546 A1 | 6/2012 | Kanikanti et al. | |
| 2015/0150985 A1 | 6/2015 | Kanikanti et al. | |
| 2017/0182118 A1 | 6/2017 | Kanikanti et al. | |

FOREIGN PATENT DOCUMENTS

| | | |
|---|---|---|
| DE | 102008022520 | 11/2009 |
| DE | 102009012423 | 9/2010 |
| WO | WO-9319053 | 9/1993 |
| WO | WO-0200202 | 1/2002 |
| WO | WO-2009135593 | 11/2009 |
| WO | WO-2013092558 | 7/2013 |

OTHER PUBLICATIONS

"Kollidon® Polyvinylpyrooline excipients for the pharmaceutical industry," BASF, The Chemical Company, Mar. 2008, 9th revised edition, p. 207-211 (Year: 2008).*
Baronsky, J. (2009) "The Study of Different Solid Forms of Emodepside," *European Journal of Pharmaceutics and Biopharmaceutics*, 71:88-99.
Buhler, V. (Mar. 1998) "*Kollidon, Polyvinylpyrrolidone for the Pharmaceutical Industry*," BASF 4th edition, 288 pages.
"Dipylidium caninum," downloaded from www.cdc.gov/parasites on Apr. 28, 2017, 3 pages.
International Search Report, dated Mar. 5, 2013 for PCT Application No. PCT/EP2012/075909, filed Dec. 18, 2012, 4 pages.
International Preliminary Report on Patentability, dated Jun. 24, 2014 for PCT Application No. PCT/EP2012/075909, filed Dec. 12, 2012 6 pages. (English Translation).
International Written Opinion, dated Jun. 21, 2014 for PCT Application No. PCT/EP2012/075909, filed Dec. 12, 2012 5 pages. (English Translation).
Kachi, S. (1998) "Effects of Amorphous and Polymorphs of PF1022A, a New Antinematode Drug, on *Angiostrongylus costaricensis* in Mice," *Jpn. J Pharmacol.* 77:235-245.
Lange, P. (May 1, 2011) "Emodepsid Bestimmung des Resorptionsortes and.Formulierungskonzepte zur Verbesserung der BioverfUgbarkeit," *Inaugural Dissertation Heinrich Heine University*, Dusseldorf pp. 1-112.
"Surfactants and Its Application in Pharmaceuticals: An Overview" downloaded from PharmaTutor.org on Aug. 31, 2015, pp. 1-12.
The Merck Veterinary Manual, "Heartworm Disease," *Merck Manuals*, downloaded on Apr. 22, 2015 from www.merckvetmanual.com/mvm/circulatory_system/heartworm_disease/overview_of_heartworm_disease.html?qt=sc=&alt=.

* cited by examiner

*Primary Examiner* — Christina Bradley
(74) *Attorney, Agent, or Firm* — Morrison & Foerster LLP

(57) ABSTRACT

The invention relates to preparations comprising amorphous emodepside in a polyvinylpyrrolidone matrix, pharmaceuticals comprising such preparations, and their use against endoparasites in animals or humans.

8 Claims, No Drawings

PREPARATIONS CONTAINING AMORPHOUS EMODEPSIDE

CROSS REFERENCE TO RELATED APPLICATIONS

This application is a continuation application of U.S. patent application Ser. No. 15/397,923, filed Jan. 4, 2017, which is a continuation application of U.S. patent application Ser. No. 14/365,841, which adopts the international filing date of Dec. 18, 2012, now U.S. Pat. No. 9,539,331, which is the National Phase application under 35 U.S.C. § 371 of International Application No. PCT/EP2012/075909, filed Dec. 18, 2012, which claims priority benefit to European Application No. 11194878.2, filed Dec. 21, 2011, the disclosures of each of which are hereby incorporated by reference in their entireties for all purposes.

The invention relates to preparations comprising amorphous emodepside in a polyvinylpyrrolidone matrix, pharmaceuticals comprising such preparations, and their use against endoparasites in animals or humans.

The cyclic depsipeptide emodepside, which has anthelmintic activity, is known from WO 93/19053. A variety of application forms have already been described, for example starch-based extrudates (WO 02/00202), or a solid dosage form with delayed release (WO 2009/135593 A2).

Kachi et al. (Jpn. J. Pharmacol. 77 (1998) 235-245) describes the amorphous and polymorphous crystalline forms of the cyclooctadepsipeptide PF1022A.

Schütte (PhD thesis, Bonn 2004) describes "Untersuchungen zur Komplexierbarkeit von pharmazcutischen Wirkstoffen mit Amylose durch Extrusion mit Hochamylosestärken" [Studies on the complexability of pharmaceutical active substances with amylose by extrusion with high-amylose starches]. Also described therein are emodepside extrudates in which starch was used as the base.

Emodepside is a sparingly soluble drug substance with poor permeability. The solubility in water in the range of pH 4-10 is 5-7 mg/l.

Said active substances frequently have poor bioavailability. There is therefore a need for emodepside preparations with improved bioavailability.

It has now been found that amorphous emodepside in specific matrices has a better solubility in water and very good bioavailability in comparison with crystalline emodepside.

The invention relates to preparations comprising emodepside in amorphous form in a polyvinylpyrrolidone matrix.

The invention furthermore relates to pharmaceuticals comprising such preparations.

The invention furthermore relates to the use of the preparations according to the invention or of the pharmaceuticals comprising the preparations according to the invention for controlling endoparasites in humans or animals.

The INN emodepside represents the compound with the systematic name: cyclo[(R)-lactoyl-N-methyl-1-leucyl-(R)-3-(p-morpholinophenyl)lactoyl-N-methyl-1-leucyl-(R)-lactoyl-N-methyl-1-leucyl-(R)-3-(p-morpholinophenyl)lactoyl-N-methyl-1-leucyl. Emodepside is described in WO 93/19053 and has the following formula:

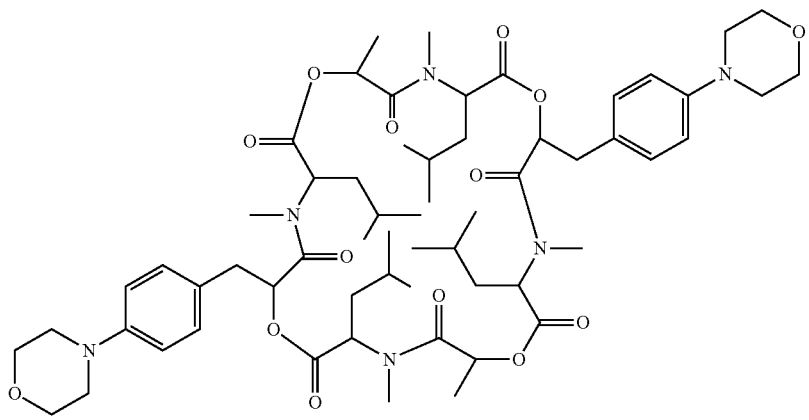 [SMILES: CC(C)CC1C(=O)OC(Cc2ccc(N3CCOCC3)cc2)C(=O)N(C)C(CC(C)C)C(=O)OC(C)C(=O)N(C)C(CC(C)C)C(=O)OC(Cc2ccc(N3CCOCC3)cc2)C(=O)N(C)C(CC(C)C)C(=O)OC(C)C(=O)N1C]

In principle, the preparations according to the invention may comprise further active substances.

Depending on the structure, active substances can be present in stereoisomeric forms or as stereoisomer mixtures, for example as enantiomers or as a racemat. The active substance emodepside has a total of 8 chiral C atoms—4 1 leucine units, 2 D-lactic acid units and 2 D-polylactic acid units. However, the synthesis is anenatioselective, so that the fermentation process only generates the one enantiomer of PF1022A.

In the preparations according to the invention, the emodepside is present in the amorphous state. Amorphous means that the atoms are present in an unordered structure. In the case of a crystalline substance, or in crystalline zones, the atoms have both a short-range order and a long-range order. Amorphous material, in contrast, only has a short-range order. The degree of crystallization of the active substance can be determined for example with the aid of dynamic differential calorimetry or x-ray diffractometry.

In the case of a calorimetric measurement, it is the melting enthalpy, in other words the energy required for melting the crystals, that is measured. If the active substance is present in a completely amorphous state, no change in the endothermal enthalpy can be measured upon heating.

When using x-ray diffraction as the measuring method, it is the distances between the molecular chains which are measured. In the amorphous state, no regular distances exist, which results in a broad distribution and no clear peaks in the diffractogram.

Other possibilities of checking the amorphous state are density measurement, x-ray diffraction, infrared spectroscopy and nuclear-resonance spectroscopy.

In the preparations according to the invention, a proportion of at least 50% by weight, preferably at least 70% by weight, especially preferably at least 80% by weight, very specially preferably at least 90% by weight, of the emodepside is present in the amorphous state, the percentages being based on the total amount of emodepside.

In case of doubt, the amorphous emodepside content is determined by dynamic differential calorimetry.

The emodepside is present in a polyvinylpyrrolidone matrix. Suitable "polyvinylpyrrolidones" are not only pure polyvinylpyrrolidones, but also their derivatives or mixtures of polyvinylpyrrolidones and polyvinylpyrrolidone derivatives.

Polyvinylpyrrolidones (povidones, PVPs) are commercially available hydrophilic polymers. Various types of PVPs are obtainable. PVPs with a relatively low molecular weight are conventionally employed as binders for tablets. In an aqueous medium, PVPs will swell and erode.

The polyvinylpyrrolidones or polyvinylpyrrolidone derivates employed are preferably water-soluble. As a rule, they are linear, non-crosslinked polyvinylpyrrolidones or polyvinylpyrrolidone derivatives.

The pure polyvinylpyrrolidones or polyvinylpyrrolidone derivatives employed in accordance with the invention usually have a K value in the range of from 12 to 90, preferably 12 to 30.

The K value of the polyvinylpyrrolidones or polyvinylpyrrolidone derivatives is in a relationship with the viscosity and the molecular weight and can be determined by methods known per se. In case of doubt, the information on the K value found in the European Pharmacopeia (Ph. Eur.) will be used.

Preferably, the pure polyvinylpyrrolidones have a K value of from 12 to 90, especially preferably from 12 to 25, very especially preferably from 12 to 17.

The polyvinylpyrrolidone derivatives usually polyvinylpyrrolidone copolymers. In the case of the polyvinylpyrrolidone copolymers, polymers with a K value of 25-30 will preferably be used.

A preferred polyvinylpyrrolidone derivative is copovidone (for example Kollidon VA 64 from BASF). This is a vinylpyrrolidone/vinyl acetate copolymer in the ratio of 6:4 with a K value of approximately 30.

The preparation usually comprises at least 50% by weight, preferably at least 66% by weight, especially preferably 75% by weight, of polyvinylpyrrolidone.

Details on the abovementioned polyvinylpyrrolidones, polyvinylpyrrolidone derivatives and certain mixtures can be found in the following book: V. Bühler, "Kollidon, Polyvinylpyrrolidone for the pharmaceutical industry", 9th revised edition, BASF Pharma ingredients, Germany, 2008.

At least two methods which are known per se exist for preparing the preparations according to the invention: solvent coprecipitation and melt extrusion.

In the case of solvent coprecipitation, emodepside together with the polymer is dissolved in the solvent, and the solvent is subsequently removed again, for example with reduced pressure and, optionally, elevated temperature. Suitable are solvents and solvent mixtures in which both the active substance and the polymer will dissolve. Substances which are suitable for the preparations according to the invention are, for example, ethanol, acetonitrile, methanol, acetone and isopropanol or their mixtures. The polymers employed in solvent coprecipitation are preferably polyvinylpyrrolidones with a K value of between 12 and 30, preferably 12 and 17, since it is easier to remove the solvent from those than from polyvinylpyrrolidones with a greater K value.

In the case of melt extrusion, the active substance is mixed with the polymer and transferred into an extruder. The extrusion temperature is below the melting point of the active substance. In the case of emodepside, the extrusion may take place between 80 and 190° C., preferably between 140 and 180° C.

The melting point of the thermodynamically most stable emodepside modification is 192° C. During the extrusion, emodepside dissolves in the polymer, and upon cooling it precipitates in the amorphous state. In general, preferred polyvinylpyrrolidones are those with a low glass transition temperature so as not to pose a risk to the stability of the active substance. In addition, it must not be too low so as to ensure a certain degree of storage stability. Polymers which can be recommended are those with a glass transition temperature of at least 80° C., but markedly below the melting point of emodepside, that is 80° C. to 160° C., preferably 80° C. to 140° C. The glass transition temperature of polyvinylpyrrolidone with a K value of 12 is approximately 90° C. and with a K value of 25 approximately 155° C.

In the case of melt extrusion, it is possible to additionally add surfactants to the system. Surfactants which are suitable in principle are customary pharmaceutically acceptable pulverulent or liquid surfactants. Examples which may be mentioned are: polyoxyethylene glycerol ricinoleate 35, macrogol glycerol hydroxystcarate 40, but also bile salts, lecithins and non-ionic surfactants such as sodium dodecyl sulphate. Other examples which may be mentioned are the polysorbate 20, 60 or 80 and poloxamers.

The preparations according to the invention may be used directly per se, or else they are processed with addition of other adjuvants. In this context, they are present in the form of granules or in the form of a powder, preferably following a grinding step, both for direct use and for processing.

"Pharmaceuticals" for the purpose of the present invention may be the preparations themselves or else compositions which, in addition to the preparations, also comprise pharmaceutically acceptable adjuvants.

Oral pharmaceutical forms which are suitable are powders, granules, suspensions, capsules or tablets, with tablets being preferred.

Possible adjuvants which may be mentioned are: fillers, glidants, lubricants, disintegrants, surfactants and the like.

Fillers which are suitable are fillers which are conventionally used for solid preparations (for example tablets), such as, for example, pharmaceutically employed starches, for example potato, wheat, maize and rice starch, various mono- and disaccharides, for example glucose, lactose and sucrose, and the sugar alcohols mannitol and sorbitol. Colloidal carbonates such as calcium carbonates, hydrogencarbonates, sodium chloride, aluminium oxides, silicas, clays and phosphates (especially calcium phosphates) may also be employed, it also being possible for different fillers to be combined with each other. Fillers having additional drybinding properties which are used arc celluloses, preferably microcrystalline cellulose. The total amount of filler(s) is usually 5-80% (m/m), preferably 10 to 70% (m/m), especially preferably 20 to 50% (m/m).

Furthermore, the solid pharmaceutical preparations according to the invention may, besides the active substance(s) and other abovementioned constituents, additionally comprise further adjuvants. Glidants which are used are, for example, colloidal silica, hydrogenated vegetable oils, stearic acid, talc or their mixtures, optionally in amounts of from usually 0.1 to 2%, preferably 0.5-1.5% (m/m). Lubricants, such as, for example, magnesium stearate, are optionally present in amounts of from usually 0.3-2% (m/m), preferably 0.5 to 1.5 (m/m). In addition, it is possible to add, to the formula, disintegrants such as, for example, croscarmellose sodium in amounts of usually 1-10% (m/m). However, higher concentrations such as 10-40% may also be used. Surfactants, for example sodium dodecylsulphate, usually 0.1-1% (m/m), preferably 0.5-1% (m/m), may be added to improve wetting. Further surfactants which may be incorporated are the non-ionic surfactants polyoxyethylene glycerol ricinoleate 35, macrogol glycerol hydroxystearate 40, polyoxylated sorbitan monooleate, sorbitan monostearate, ethyl alcohol, glycerol monostearate, polyoxyethyl stearate and alkylphenol propyl glycol ether, the ampholytic surfactants disodium N-lauryl-β-iminodipropionate and lecithin, and the anionic surfactants sodium lauryl sulphate, fatty alcohol ether sulphate and mono/dialkyl polyglycol ether orthophosphoric ester monoethanolamine salts.

To improve the palatability, aromas and/or flavourings may furthermore be added to the formula.

The preparations according to the invention can be prepared for example by mixing or granulating the components and then compressing the product to give tablets. Preferred in this context is the direct tableting of the starting materials, that is to say that all starting materials are mixed and that the mixture is directly compressed to give tablets, without further process steps such as granulation or the like.

The preparations according to the invention, or the pharmaceuticals according to the invention, are suitable for controlling pathogenic endoparasites which are found in humans and in animal keeping and animal breeding in livestock, breeding stock, zoo animals, laboratory animals, experimental animals and pets, while having favourable toxicity to warm-blooded species. They can be employed against all or individual developmental stages of the pests and against resistant and normally-sensitive endoparasite isolates. By controlling the pathogenic endoparasites, it is intended to reduce disease, deaths and reduced performance (for example in the production of meat, milk, wool, hides, eggs, honey and the like), so that more economical, simpler and healthier animal keeping is made possible by employing the active substances. The pathogenic endoparasites include helminths such as Platyhelmintha (in particular Monogenea, Cestoda and Trematoda), Nematoda, Pentastoma and Acanthocephala. Examples which may be mentioned are:

Monogenea: for example: *Gyrodactylus* spp., *Dactylogyrus* spp., *Polystoma* spp.

Cestoda: From the order Pseudophyllidea, for example: *Diphyllobothrium* spp., *Spirometra* spp., *Schistocephalus* spp., *Ligula* spp., *Bothridium* spp., *Diphlogonoporas* spp.

From the order Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematoda: from the class Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp. *Echinostoma*. spp., *Echinaparyphium* spp., *Echinochasmus* spp., *Hypoderaeum* spp., *Fasciola* spp., *Fasciolides* spp., *Fasciolopsis* spp., *Cyclocoelum* spp., *Typhlococlum* spp., *Paramphistomum* spp., *Calicophoron* spp., *Cotylophoron* spp., *Gigantoeotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

Nematoda: From the order Trichinellida, for example: *Trichuris* spp., *Capillaria* spp., *Trichomosoides* spp., *Trichinella* spp.

From the order Tylenchida, for example: *Micronema* spp., *Strongyloides* spp.

From the order Rhabditina, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylieostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystoeaulus* spp., *Pneumostrongylus* spp., *Spicocaulus* spp., *Elaphostrongylus* spp., *Parelaphostrongylus* spp., *Crenosoma* spp., *Paracrenosoma* spp *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Acanthocephala: From the order Oligaeanthorhynchida, for example: *Macracanthorhynchus* spp., *Prosthenorchis* spp.; from the order Polymorphida, for example: *Filicollis* spp.; from the order Monilifointida, for example: *Montliformis* spp.

From the order Echinorhynchida, for example: *Acanthocephalus* spp., *Echinorhynchus* spp., *Leptorhynchoides* spp.

Pentastoma: From the order Porocephalida, for example: *Linguatula* spp.

In accordance with a preferred embodiment, the preparations according to the invention, or the pharmaceuticals according to the invention, are employed for controlling heart worm, *Dirofilaria immitis*.

Animals may be fish, reptiles, birds or in particular mammals.

The livestock and breeding stock include mammals such as, for example, cattle, horses, sheep, pigs, goats, camels, water buffalo, monkeys, rabbits, fallow deer, reindeer, fur-bearing animals such as, for example, mink, chinchilla, racoon, birds such as, for example, chickens, geese, turkeys, ducks, ostriches, fish such as trout, salmon, carp, perch, pikes, eels.

Laboratory animals and experimental animals include mice, rats, guinea pigs, golden hamsters, dogs and cats.

The pets include dogs and cats.

Preferred in accordance with the invention is the use in animals, but the use in humans is also possible in principle.

The application may be either prophylactic or else therapeutic.

The preparations according to the invention with amorphous emodepside have good bioavailability. They show a high plasma level concentration and good data as regards the area under the concentration-time curve of emodepside in the blood.

EXAMPLES

1. Coprecipitate Prepared by Solvent Method

When preparing a solvent coprecipitate, emodepside and polyvinylpyrrolidone with a K value of 12, 17 or 25 are mixed and dissolved in ethanol or in a solvent mixture of acetone and isopropanol. After everything has dissolved, the solution is transferred to a sheet, and the solvent is stripped off at elevated temperature and reduced pressure in a vacuum drying oven. Thereafter, the coprecipitate thus obtained is scrapped off the sheet and ground. The powder thus obtained may now be administered either directly, for example filled into capsules, or, after processing, in the form of tablets.

Coprecipitates of the following compositions were prepared, where the compositions were in each case converted to a theoretical total weight of 100 g of the coprecipitate. In each case three compositions with polyvinylpyrrolidone-12, -17 and -25 were prepared for each example:

Example 1

25 g Emodepside
75 g Polyvinylpyrrolidone-12, -17 or -25
Isopropano/acetone 1:1 (until everything has dissolved)

Example 2

50 g Emodepside
50 g Polyvinylpyrrolidone-12, -17 or -25
Isopropanol/acetone 1:1 (until everything has dissolved)

Example 3

9.09 g Emodepside
90.91 g Polyvinylpyrrolidone-12, -17 or -25
Isopropanol/acetone 1:1 (until everything has dissolved)

Example 4

25 g Emodepside
75 g Polyvinylpyrrolidone-12, -17 or -25
Ethanol (until everything has dissolved)

Example 5

33.33 g Emodepside
66.67 g Polyvinylpyrrolidone-12, -17 or -25
Ethanol (until everything has dissolved)

Example 6

9.09 g Emodepside
90.91 g Polyvinylpyrrolidone-12, -17 or -25
Ethanol (until everything has dissolved)

2. Tablet Formulation:

When the coprecipitate is processed to give tablets, it is mixed with the tableting aids microcrystalline cellulose, croscarmellose sodium, highly-dispersed silica, sodium dodecyl sulphate and magnesium stearate and the mixture is compressed to give tablets.

The following tablet formulation may be mentioned by way of example:

Example 7

(a 100 g batch is composed of)
21.3 g Solvent coprecipitate as per Example 1 with polyvinylpyrrolidone-12
32 g Microcrystalline cellulose
42.6 g Croscarmellose sodium
0.8 g Sodium dodecyl sulphate
1.6 g Highly-dispersed silica
1.6 g Magnesium stearate.

3. Coprecipitate Prepared by Melt Extrusion

In the case of the preparation which is prepared by melt extrusion (extruded coprecipitate), emodepside and the polyvinylpyrrolidone copolymer (copovidone, for example Kollidon VA 64 from BASF) are mixed and transferred into the extruder. If required, a surfactant, for example, polyoxyethylene glycerol ricinoleate 35, can be introduced via liquid metering. This mixture is extruded at 160° C. Extrusion at 180° C. is also possible. The resulting emodepside/polyvinylpyrrolidone extrudates are cooled and ground. Again, here the powder may be administered as such or processed to give tablets.

Extruded coprecipitates of the following compositions were prepared, while the compositions were in each case converted to a theoretical total weight of 100 g of the extruded coprecipitate:

Example 8

20 g Emodepside
70 g Copovidone
10 g Polyoxyethylene glycerol ricinoleate 35

Example 9

9.09 g Emodepside
80.91 g Copovidone
10 g Polyoxyethylene glycerol ricinoleate 35

Example 10

20 g Emodepside
80 g Copovidone

4. Tablet Formulation

The preparation which is obtained by melt extrusion, too, can be processed in the same manner to give tablets. An example which may be mentioned is the following tablet mixture:

Example 11

(a 100 g batch is composed of):
25.3 g Extruded coprecipitate according to Example 8
30.4 g Microcrystalline cellulose
40.5 g Croscarmellose sodium
0.8 g Sodium dodecyl sulphate
1.5 g Highly-dispersed silica
1.5 g Magnesium stearate.

Biological Example

A. Study into the Pharmacokinetics:

The tablets of Example 7 (with 10 mg emodepside and a total weight of 87.5 mg) were administered to 10 dogs and the tablets of Example 11 (with 10 mg emodepside and a total weight of 197.5 mg) were administered to 4 dogs, in each case orally. By way of comparison, an emodepside solketal solution (10% m/m) was administered to 4 dogs, in each case orally. For all formulations, the dosage was 1 mg/kg body weight. Thereafter, blood was taken from the dogs at regular intervals up to 72 h after the application. The values of the maximum plasma level concentration Cmax were improved markedly by using the active substance in the amorphous state: from 93 µg/l in the case of the emodepside solketal solution to 187 µg/l for tablets of Example 11 and 246 µg/l for table of Example 7. The AUC(0-24 h) values were instead of 508 µg/l in the case of the solution 825 µg/l for the tablets of Example 11 and 1129 µg/l for the tablets of Example 7, respectively.

The invention claimed is:

1. A preparation comprising emodepside in amorphous form in a polyvinylpyrrolidone matrix, wherein the polyvinylpyrrolidone matrix contains a polyvinylpyrrolidone derivative having a K value in the range of between 12 and 30.

2. The preparation according to claim 1, wherein the polyvinylpyrrolidone derivative is copovidone.

3. The preparation according to claim 2, wherein the polyvinylpyrrolidone derivative is a vinylpyrrolidone/vinyl acetate copolymer in the ratio of 6:4 with a K value of approximately 30.

4. A method for treating or preventing an endoparasite comprising administering to a human or animal in need thereof an effective amount of a pharmaceutical composition comprising emodepside in a polyvinylpyrrolidone matrix, wherein at least 50% of the emodepside is in an amorphous form.

5. The method according to claim 4, wherein the endoparasite is a helminth.

6. The method according to claim 5, wherein the helminth is a Nematoda.

7. The method according to claim 6, wherein the endoparasite is a Nematoda selected from the group consisting of the order Trichinellida, the order Tylenchida, the order Rhabditina, and the order Spirurida.

8. The method according to claim 7, wherein the Nematoda is selected from the group consisting of *Trichuris* spp., *Trichinella* spp., *Strongyloides* spp., *Ancylostoma* spp., *Enterobius* spp., *Ascaris* spp., *Toxascaris* spp., *Dracunculus* spp., *Loa* spp., *Brugia* spp., *Wuchereria* spp., and *Onchocerca* spp.

* * * * *